United States Patent [19]

Wells

[11] Patent Number: 5,086,254
[45] Date of Patent: Feb. 4, 1992

[54] MICROWAVE EXCITED HELIUM PLASMA PHOTOIONIZATION DETECTOR

[75] Inventor: Gregory J. Wells, Suisun, Calif.

[73] Assignee: Varian Associates, Inc., Palo Alto, Calif.

[21] Appl. No.: 26,934

[22] Filed: Mar. 17, 1987

Related U.S. Application Data

[63] Continuation of Ser. No. 672,646, Nov. 19, 1984, abandoned, which is a continuation-in-part of Ser. No. 522,081, Aug. 11, 1983, abandoned, which is a continuation of Ser. No. 733,854, May 13, 1985, Pat. No. 4,684,807.

[51] Int. Cl.$^5$ .................................................. H01J 7/24
[52] U.S. Cl. .................................. 315/111.21; 315/39; 315/111.71
[58] Field of Search ............... 315/39, 111.21, 111.71, 315/116.31; 250/303, 381, 379; 356/313; 324/58.5 A, 465, 464, 469

[56] References Cited

U.S. PATENT DOCUMENTS

| | | | |
|---|---|---|---|
| 2,975,330 | 3/1961 | Bloom | 315/115 |
| 3,336,493 | 8/1967 | Lambert | 313/231 |
| 3,418,514 | 12/1968 | Sternberg | 313/231.71 |
| 3,610,759 | 10/1971 | Wood | 315/231 |
| 3,933,432 | 1/1976 | Driscoll | 250/423 |
| 3,973,186 | 8/1976 | Vehara et al. | 324/58.5 A |
| 4,251,726 | 2/1981 | Alvarez | 350/358.1 |
| 4,266,196 | 5/1981 | Kawazoe et al. | 313/231.71 |
| 4,309,187 | 1/1982 | Dodge et al. | 315/111.01 |
| 4,393,333 | 7/1983 | Sakudo et al. | 315/39 |
| 4,398,152 | 8/1983 | Leveson | 324/465 |
| 4,409,520 | 10/1983 | Koike et al. | 315/39 |
| 4,529,911 | 7/1985 | Hutter | 315/39 |
| 4,532,219 | 7/1985 | Hagen et al. | 315/111.41 |

FOREIGN PATENT DOCUMENTS 989614 4/1965 United Kingdom .

OTHER PUBLICATIONS

Anal. Chem, 1981, 1336–1340, "High Resolution Gas Chromatography of Trialkyllead Chlorides with an Inert Solvent Venting" Estes et al.

Primary Examiner—Michael Razavi
Attorney, Agent, or Firm—Peter J. Sgarbossa

[57] ABSTRACT

A photoionization detector for detecting effluents from a gas chromatographic column has a microwave induced helium plasma as the photon source. Since the source plasma may be at atmospheric pressure and need not be sealed, energy loss due to transmission of photons through a window can be eliminated. Use of alternating electromagnetic fields instead of a direct current discharge obviates the problems of anode sputtering.

12 Claims, 3 Drawing Sheets

MICROWAVE EXCITED HELIUM PLASMA PHOTOIONIZATION DETECTOR

This application is a continuation of application Ser. No. 672,646, filed Nov. 19, 1984 now abandoned which is a continuation-in-part of Ser. No. 522,081 filed Aug. 11, 1983 which was abandoned, which is a C-I-P of Ser. No. 733,854, filed May 13, 1985, now issued as U.S. Pat. No. 4,684,807.

BACKGROUND OF THE INVENTION

This invention relates generally to a method of detecting effluents from a gas chromatographic column by photoionization and in particular to a photoionization detector of which the photon source is a microwave induced helium plasma.

The photoionization detector is generally constructed in such a manner that photons are generated by a discharge in the presence of a discharge gas and guided into a detecting section to ionize the sample gas, the sample gas ions being collected by an electrode in the detection section for the measurement of ionization current. While compounds such as $O_2$, $N_2$, $H_2$, $H_2O$, $SO_2$ and $NO_2$ give little or no response in a flame ionization detector, a photoionization detector is capable of detecting both inorganic and organic constituents with a high sensitivity and hence is suited for gas chromatography.

Prior art photoionization detectors can be divided generally into the following two classes, the first utilizing a low pressure discharge lamp as the photon source and the second using atmospheric pressure discharges. The disadvantage of a sealed source in the case of the former is that the highest photon energy that is available for ionization is limited to about 12eV by the transmission of the window. Since the ionization potential of $O_2$ is 12.08 eV, this means that the detector sensitivity cannot be good for this compound. $N_2$ and $H_2$ with ionization potentials respectively of 15.58 eV and 15.61 eV will not even give a response.

To overcome these limitations, atmospheric pressure discharges in helium were used as light sources including the 21.22 eV radiation from He I line. Since the discharge occurs at atmospheric pressure, no windows are necessary and this allows higher energy photons to be utilized in the ionization process. A direct current discharge detector of this type with a pointed cathode and a conical anode is disclosed, for example, in U.S. Pat. No. 3,418,514 issued to J. C. Sternberg. This approach, however, has the disadvantage that the anode is quickly destroyed by the sputtering action of the current of electrons that impinge onto its surface. This results in an increase in noise due to the arc moving around on the surface of the anode.

An attempt to overcome this problem is found in U.S. Pat. No. 4,266,196 issued to K. Kawazoe et al which describes a direct current discharge photoionization detector with a point cathode and a disk anode, the claim being that the electron current to the anode in this system is distributed around the edge of the disk and therefore that erosion and noise due to sputtering are reduced. In practice, however, this method fails because sputtering will eventually cause one particular area of the disk to have locations on the surface where the electric field strength is concentrated and hence higher than in the surrounding areas. The distributed arc will then collapse and the sputtering rate at such locations will be accelerated, causing the condensed arc to wander about the anode surface and resulting in an increased noise level.

SUMMARY OF THE INVENTION

It is therefore an object of the present invention to provide a photoionization detector with high measuring accuracy.

It is another object of the present invention to provide a photoionization detector which, operating at atmospheric pressure, has a low noise level.

According to this invention, the above and other objects are achieved and the problems of anode sputtering described above are overcome by generating high energy photons from a microwave induced plasma in helium at atmospheric pressure. The use of alternating electromagnetic fields in the microwave region (2–4 GHz) eliminates the sputtering sputtering problems since direct currents are not involved. The type of plasma used herein is often termed an electrodeless discharge because the charged species in the plasma need not come in contact directly with any electrode and can even be completely enclosed by an insulating material.

DETAILED DESCRIPTION OF THE INVENTION

Figure 1:
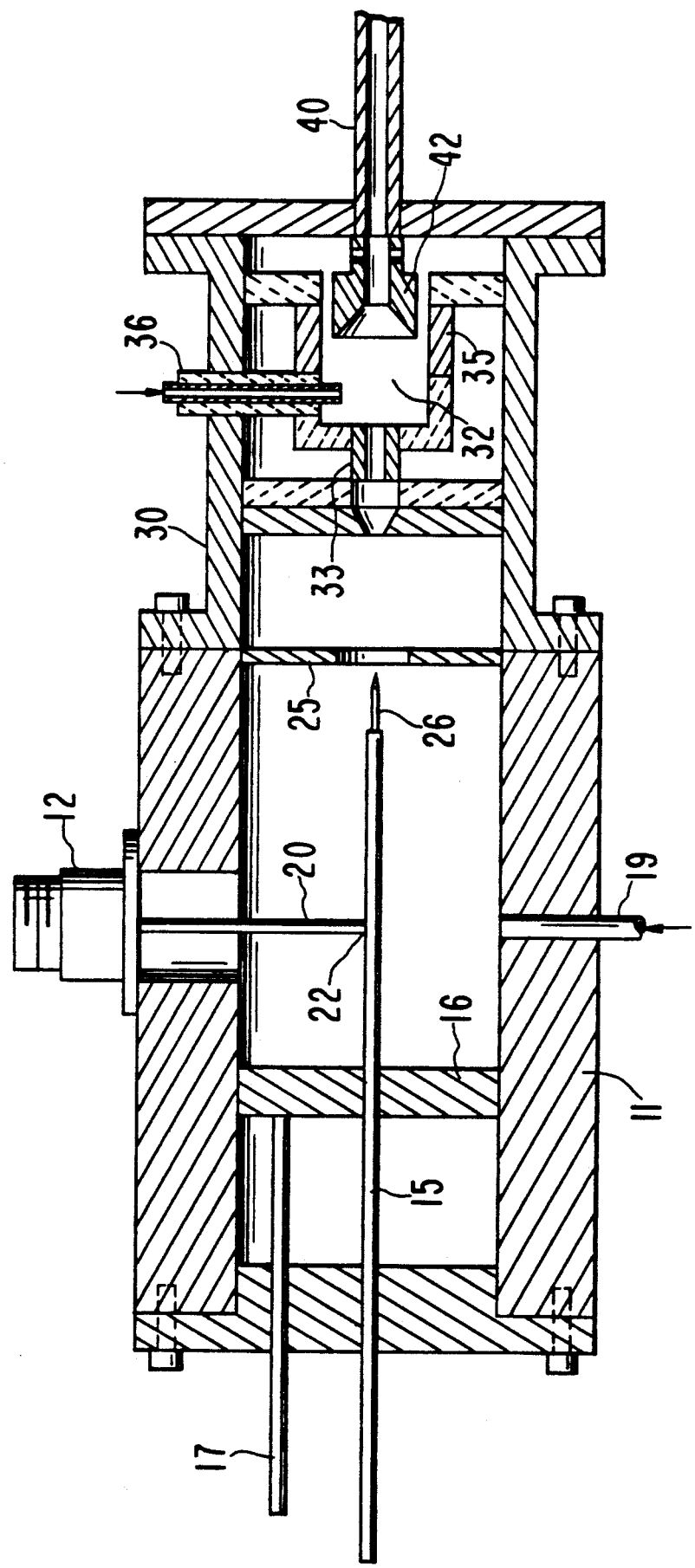
FIG. 1 is a cross-sectional view of a microwave excited plasma photoionization detector, showing schematically the construction of one embodiment of this invention.

There is shown in FIG. 1 a photoionization detector embodying the present invention including a source of plasma. The region where plasma is generated is inside a metallic cylindrical housing 11. Microwave power (2–4 GHz) enters the region through a UG 58/U connector 12 attached on the outer wall of the housing 11. A central conductor 15 in the shape of a thin rod is positioned and maintained on the symmetry axis of the cylindrical housing 11. The central conductor 15 is supported by a sliding short 16, penetrating it at the center of its piston. A handle 17 is provided to the short 16 so that the short can be moved slidably inside the housing 11. The housing is further provided with a duct 19 with an opening on a side. The duct 19 is connected to a source of helium gas (not shown) for the plasma.

An inlet conductor 20 is provided so as to electrically connect the connector 12 with the central conductor 15 so that microwave power entering through the connector 12 will propagate both in forward and backward directions along the central conductor 15. When the sliding short 16 is at the position ¼ wavelength from the intersection 22 of the central conductor 15 and the inlet conductor 20, the imaginary part of the complex load impedance becomes infinite, and the result is that the power propagating along the central conductor 15 in the direction towards the sliding short 16 is reflected back towards the exit iris 25 provided at the back end of the housing 11. The real part of the complex load impedance, on the other hand, depends on the distance between the intersection 22 and the iris 25 as well as the nature of the plasma located in the iris. Since both of these factors are affected by the separation between the end of the central conductor 15 and the iris 25, this separation may be varied to adjust the real part of the impedance in most cases. When it matches the generator output impedance, there is no reflected power and this has the result that all of the input power is coupled into the plasma. Due to the coupling efficiency, a plasma in helium at atmospheric pressure can be generated with as little as 5 watts of power. The resulting plasma is suspended in the region between the central conductor 15 and the iris 25 and does not touch any surface. In this embodiment, the backward end of the central conductor 15 is shown to contain a needle 26. The sharpness of the needle point has the effect of concentrating the brightest portion of the plasma to nearly a point source.

A detector assembly 30 is disposed directly behind the iris 25, attached through a usual flange-bolt means to the housing 11. According to this embodiment, the detector assembly 30 includes a photoionization detector cell 32 which is substantially of a tubular form with a circular cross section disposed in a coaxial relationship with the central conductor 15, a tubular polarization electrode 33 with a reduced aperture and a circular cylindrical collector electrode 35. An electrically insulated inlet tube 36 for introducing the sample gas from a chromatographic column opens into the cell 32 through a side between the polarization electrode 33 and the collector electrode 35. The aperture of the polarization electrode 33, through which helium gas enters the detector cell 32, is intended to define the spatial extent of the photons entering the collector region such that the photons will be prevented from striking the collector walls and thus ejecting electrons. The reduced aperture of the polarization electrode 33 is for preventing the column effluents from back-diffusing into the plasma. The flow of helium gas entering the housing 11 through the duct 19 is also intended to prevent such back diffusion.

At the other end (distal the iris 25) of the cell 32 is an exit tube 40 for exhausting the discharge and sample gases from the cell 32. Inside the cell 32, there is also provided an exit assembly 42 with a funnel-shaped part facing the inlet tube 36 and a tubular part facing the exit tube 40. One of the purposes of the exit assembly 42 is to contour the flow at the end of the detector cell 32 so as to prevent mixing effects which may occur near the exit tube 40. Another important purpose is to trap any photons that were not absorbed by the sample gas and passed through the cell 32 so that any electrons that are ejected will not be collected. The exit assembly 42 is grounded and electrically isolated from the collector cell 32 and the collector electrode 35.

Figure 2:
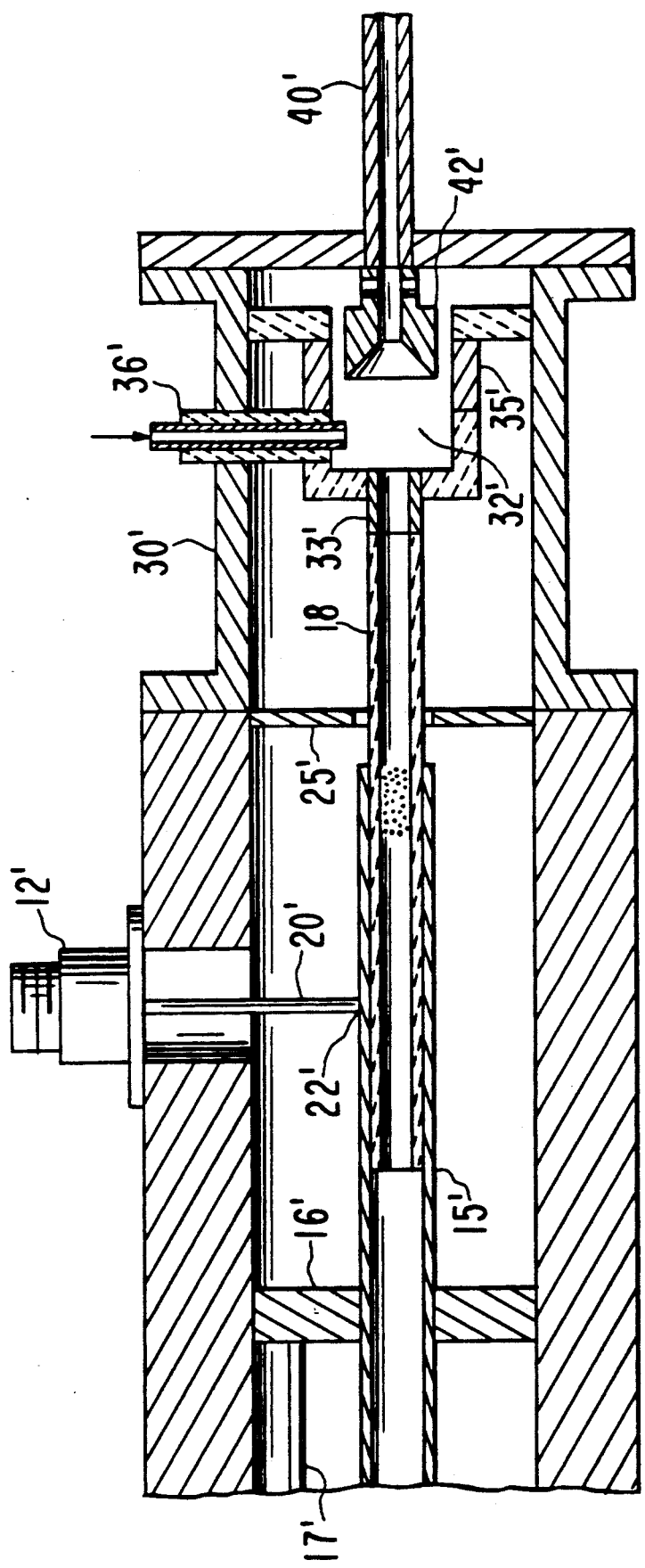
FIG. 2 is a cross-sectional view of a microwave excited plasma photoionization detector, showing schematically the construction of another embodiment of this invention.

An alternate embodiment of the present invention is shown in FIG. 2 wherein corresponding components are assigned like numerals. In this embodiment, a central conductor 15' is tubular in structure and is intended for helium plasma support gas to flow through. An electrically insulated tube 18, for example, of a ceramic material is supported by it for confining the plasma. This insulative tube 18 passes through the iris 25' and connects directly to the polarization electrode 33'. This design results in a higher plasma density and hence a brighter photon source, eliminating the need to seal the microwave structure 11' against the influx of air. The presence of air outside the insulated tube 18 has the advantage of preventing the formation of a plasma outside of the tube; which would happen if the structure 11' were filled with helium.

Figure 4:
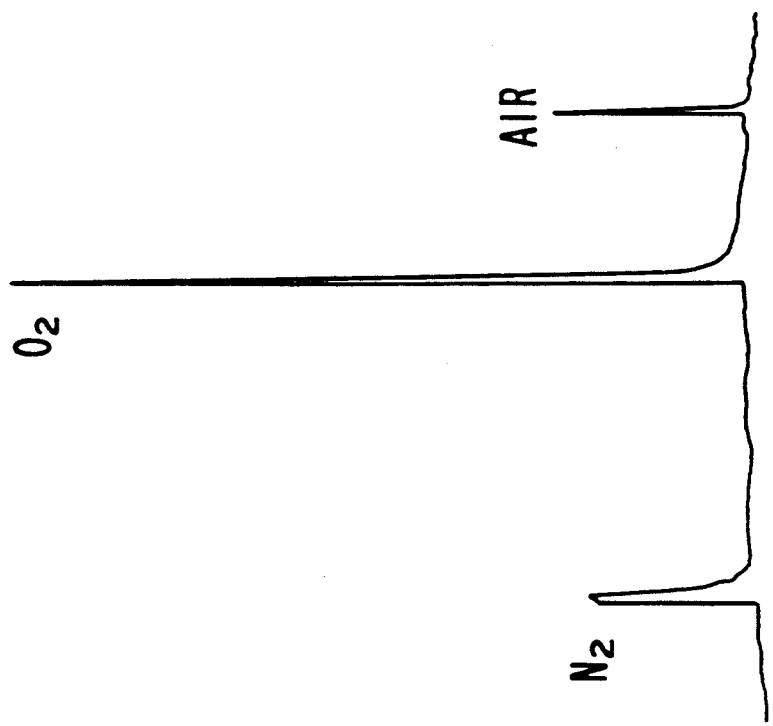
FIG. 4 shows an example of detection of oxygen, nitrogen and air by using a detector of this invention.
Figure 3:
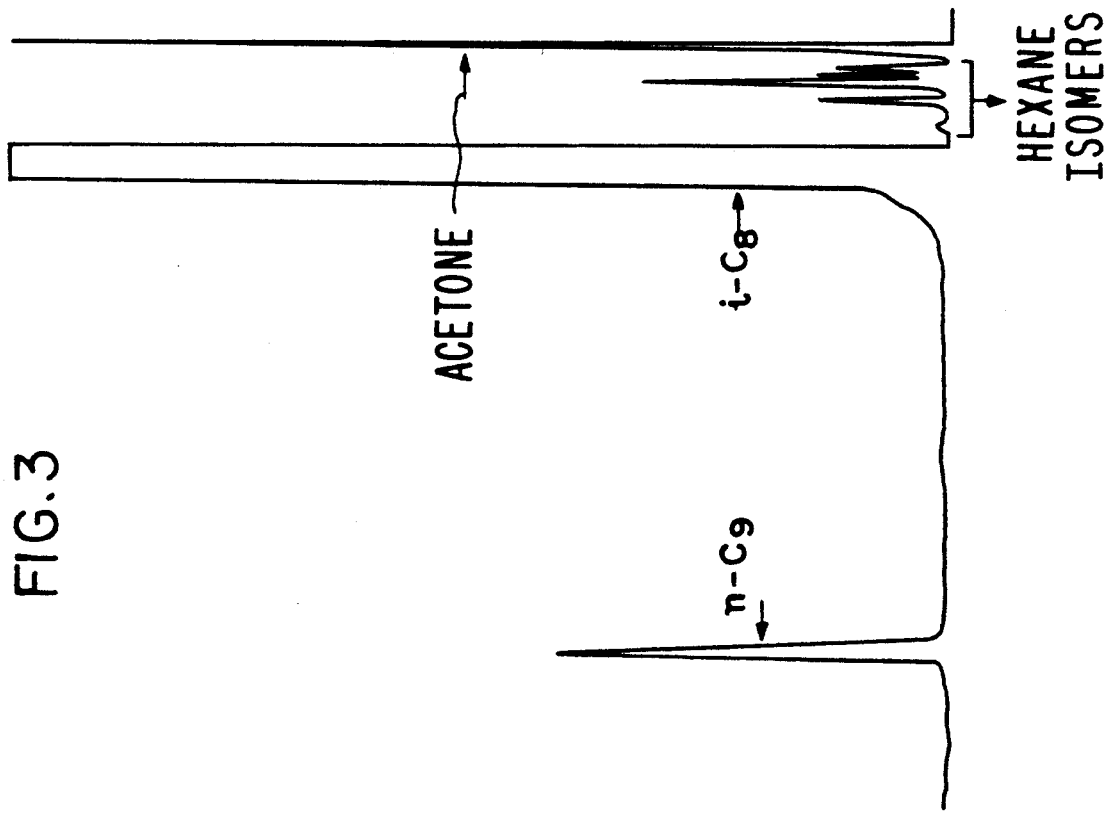
FIG. 3 shows an example of detection of a mixture of hydrocarbons by using a detector of this invention.

FIG. 3 shows the detection of a mixture of hydrocarbons. The sensitivity for carbon based on nonane was found to be 0.627 coul/gC at 5 watts of power and 1.57 coul/gC when 20 watts was used. This should be compared to 0.015 coul/gC which was obtained by using a flame ionization detector. FIG. 4 shows the detection of oxygen, nitrogen and air.

This invention was described above in terms of only two embodiments but the disclosure given above is intended to be illustrative rather than as limiting, and it is therefore intended to be interpreted broadly. For example, plasmas of different gases may be substituted and detectors of different designs may be used. FIGS. 1 and 2 are intended to be schematic and hence do not represent preferred dimensional relationships. The scope of this invention is limited only by the following claims.

What is claimed is:

1. A photoionization detector operating at substantially atmospheric pressure comprising,
    a photon source comprising a microwave-powered plasma generating means, said plasma comprising Helium, said photon source having a first windowless aperture through which photons propagate,
    a photoionization cell comprising a collector electrode, inlet means for receiving a flow of sample gas, outlet means for allowing said sample gas to exit and a second windowless aperture through which photons emitted from said photon source enter said photoionization cell,
    said photoionization cell and said photon source being adjacent and abutting each other and said first and second windowless apertures being aligned and in registration, and
    means for continuously flowing said Helium into said photon source, whereby a slight overpressure of Helium develops within said photon source and whereby the slight overpressure causes Helium to flow through said first windowless aperture into said photoionization cell.

2. The photoionization detector of claim 1 wherein said photon source comprises a tubular housing defining a symmetry axis and an elongate central conductor on said symmetry axis.

3. A photoionization detector operating at substantially atmospheric pressure comprising,
    a photon source comprising a microwave-powered Helium plasma generating means including a tubular housing defining a symmetry axis and an elongate central conductor on said symmetry axis, said housing having a first windowless aperture through which photons propagate,
    said photon source further including an inlet conductor having two ends and being connected to a source of microwave power at one end and connected to said central conductor at the other end, and a sliding short in electrical contact with said central conductor adapted to adjustably move longitudinally along said symmetry axis,
    a photoionization cell comprising a collector electrode, inlet means for receiving a flow of sample gas, outlet means for allowing said sample gas to exit and a second windowless aperture through which photons emitted from said photon source enter said photoionization cell, said photoionization cell and said photon source being adjacent and abutting each other and said first and second windowless apertures being in registration.

4. A photoionization detector operating at substantially atmospheric pressure comprising, a photon source comprising a microwave-powered Helium plasma generating means including a tubular housing defining a symmetry axis and an elongate central conductor on said symmetry axis, said housing having a first windowless aperture through which photons propagate, a photoionization cell comprising a collector electrode, inlet means for receiving a flow of sample gas, outlet means for allowing said sample gas to exit and a second windowless aperture through which photons emitted from said photon source enter said photoionization cell, said photoionization cell and said photon source being adjacent and abutting each other and said first and second windowless apertures being in registration, and said central conductor comprising a needle on said symmetry axis which points to said photoionization cell, whereby said plasma is generated in the vicinity of said needle.

5. A photoionization detector operating at substantially atmospheric pressure comprising, a photon source comprising a microwave-powered Helium plasma generating means, including a tubular housing defining a symmetry axis and an elongate central conductor on said symmetry axis, said housing having a first windowless aperture through which photons propagate, said central conductor holding an electrically insulative tube coaxial with said symmetry axis, whereby said plasma is generated within said insulative tube, and a photoionization cell comprising a collector electrode, inlet means for receiving a flow of sample gas, outlet means for allowing said sample gas to exit and a second windowless aperture through which photons emitted from said photo source enter said photoionization cell, said photoionization cell and said photon source being adjacent and abutting each other and said first and second windowless apertures being in registration.

6. A photoionization detector operating at substantially atmospheric pressure comprising, a photon source comprising a microwave-powered plasma generating means, said plasma comprising Helium, said photon source having a first windowless aperture through which photons propagate, a photoionization cell comprising a collector electrode, inlet means for receiving a flow of sample gas, outlet means for allowing said sample gas to exit and a second windowless aperture through which photons emitted from said photon source enter said photoionization cell, and a funnel-like structure adapted to contour the flow of sample gas within the photoionization cell, said photoionization cell and said photon source being adjacent and abutting each other and said first and second windowless apertures being in registration, and means for continuously flowing said Helium into said photon source, whereby a slight overpressure of Helium develops within said photon source and whereby the slight overpressure causes Helium to flow thorough said first windowless aperture into said photoionization cell.

7. The photoionization detector of claim 6 wherein said funnel-like structure is made of electrically conductive material and wherein the mouth of said funnel is oriented towards said second windowless aperture to intercept any photons entering said photoionization cell which pass through said sample gas unabsorbed, and whereby electrons ejected by said intercepted photons are trapped by said funnel.

8. A photoionization detector comprising:

a photon source comprising a microwave-powered plasma generating means, said photon source having a first windowless aperture through which photons propogate;

a photoionization cell abutting said photon source comprising a collector electrode, inlet means for receiving a flow of sample gas at substantially atmospheric pressure, outlet means for allowing said sample gas to exit and a second windowless aperture in registration with said first windowless aperture through which photons emitted from said photon source enter said photoionization cell;

said microwave-powered plasma generating means comprising a tubular housing defining a symmetry axis, said first and second windowless apertures lying on said symmetry axis, an elongate central conductor on said symmetry axis, a sliding short in electrical contact with said central conductor adapted to adjustably move longitudinally along said symmetry axis, an inlet conductor having two ends and being connected to a source of microwave power at one end and connected to said central conductor at the other end.

9. The photoionization detector of claim 8 wherein said central conductor comprises a needle on said symmetry axis which points to said photoionization cell, whereby said photon emitting plasma is generated in the vicinity of said needle.

10. The photoionization detector of claim 8 wherein said central conductor holds an electrically insulative tube coaxial with said symmetry axis.

11. The photoionization detector of claim 8 means for continuously flowing Helium into the vicinity of said central conductor means and for exhausting said Helium through said first windowless aperture and into said photoionization detector.

12. The photoionization detector of claim 8 wherein said photoionization cell further comprises a funnel-like structure adapted to contour the flow of sample gas within the photoionization cell, said funnel-like structure being made of electrically conductive material and wherein the mouth of said funnel is oriented towards said second windowless aperture to intercept any photons entering said photoionization cell which pass through said sample gas unabsorbed, whereby electrons ejected by said intercepted photons are trapped by said funnel-like structure.

* * * * *